(12) United States Patent
Moreno et al.

(10) Patent No.: US 6,810,751 B2
(45) Date of Patent: Nov. 2, 2004

(54) METHOD AND APPARATUS FOR VASCULAR DURABILITY AND FATIGUE TESTING

(76) Inventors: Michael R. Moreno, 8811 NW. 47th Dr., Coral Springs, FL (US) 33067; James E. Moore, Jr., 9575 SW. 145th Ct., Miami, FL (US) 33186

( * ) Notice: Subject to any disclaimer, the term of this patent is extended or adjusted under 35 U.S.C. 154(b) by 143 days.

(21) Appl. No.: 10/208,497

(22) Filed: Jul. 29, 2002

(65) Prior Publication Data

US 2004/0016301 A1 Jan. 29, 2004

(51) Int. Cl.⁷ .................................................. G01N 3/20
(52) U.S. Cl. ........................................... 73/849; 73/862
(58) Field of Search .......................... 73/849, 862, 841, 73/862.391, 862.451, 862.454

(56) References Cited

U.S. PATENT DOCUMENTS

| | | | |
|---|---|---|---|
| 3,664,182 A | 5/1972 | Butler | |
| 4,381,663 A | 5/1983 | Swanson | |
| 4,941,870 A | * 7/1990 | Okada et al. | 600/36 |
| 4,972,721 A | 11/1990 | Conti | |
| 5,218,842 A | 6/1993 | Tower, Jr. et al. | |
| 5,670,708 A | 9/1997 | Vilendrer | |
| 5,792,603 A | * 8/1998 | Dunkelman et al. | 435/1.2 |
| 6,121,042 A | * 9/2000 | Peterson et al. | 435/284.1 |
| 6,663,617 B1 | * 12/2003 | Vito et al. | 606/1 |

* cited by examiner

*Primary Examiner*—Max Noori
(74) *Attorney, Agent, or Firm*—Christensen O'Connor Johnson Kindness PLLC (57) ABSTRACT

A vascular prosthesis tester (10) for inducing stresses upon a vascular prosthesis (22) having a channel extending through the vascular prosthesis is disclosed. The tester includes a pump (18) adaptable to pressurize a fluid disposed within the channel to induce a radial stress upon the vascular prosthesis. The tester may further include a bend applicator (16) operable to induce a bending stress, a torque applicator (12) operable to induce a torque, a linear force applicator (52) operable to induce a linear force, and/or a stop (28) for inducing a lateral push stress upon the vascular prosthesis. A method of fatigue testing a vascular prosthesis contained within a fluid conduit is also disclosed. The method includes injecting a fluid within the inner channel and inducing a torque, bending stress, linear stress, and/or later push stress upon the vascular prosthesis.

71 Claims, 6 Drawing Sheets

METHOD AND APPARATUS FOR VASCULAR DURABILITY AND FATIGUE TESTING

FIELD OF THE INVENTION

The present invention relates generally to the field of vascular prosthesis testing, and more particularly, to vascular prosthesis testing that simulates physiological loading conditions.

BACKGROUND OF THE INVENTION

Vascular prosthesis, such as stents, grafts, and stent-grafts are often used in the medical field to repair vascular abnormalities in a patient. In one such non-limiting example, a vascular prosthesis may be used to repair an Abdominal Aortic Aneurysm (hereinafter "AAA"). An AAA is an abnormal dilation of the abdominal part of the aorta, which is frequently fatal if ruptured. Conventional surgical repair requires a major operation. An alternative treatment strategy is known as vascular stent grafting. In vascular stent grafting, a stent-graft is positioned within the dilated portion of the aorta to reduce the pressure in the aneurysm sac. The stent-graft is a combination of a structural metal skeleton stent and an outer polyester fabric graft. The stent-graft is delivered through a catheter and is positioned using X-ray guidance and interventional radiological techniques. The successful completion of the procedure means that the aneurysm is excluded from circulation, blood is not leaked to the aneurysm, and that the stent-graft does not block any vital branch arteries.

Inasmuch as the stent-graft is placed within the aorta of the patient, the stent-graft is subjected to physiological loading conditions for the life of the stent-graft or the patient. Therefore, it is apparent that sufficient testing of the stent-graft's fatigue and durability characteristics is important. When stent-grafts were developed to treat AAA, the pre-clinical testing required involved mainly extensions of the tests required for stents intended to treat stenotic disease to AAA stent-grafts. Stents for stenotic disease are typically required to withstand only external radial compression, and the prior art fatigue tests reflect this singular requirement. The prior art devices utilized for testing stent fatigue failure feature simple straight compliant tubes in which the pressure is cycled over time to model the stresses induced by the pumping of the heart.

A testing regime limited to fluid-pressure-induced stresses fails to adequately simulate the physiological stresses exhibited upon a stent-graft, since the physiological stresses exhibited upon an AAA stent-graft are substantially more complex and varied than a stenotic stent. For example, stenotic stents are deployed over relatively short lengths of a vessel, such as a few centimeters, where the vessel remains relatively stationary. In contrast, AAA stent-grafts having lengths of 30 to 40 centimeters are deployed into vessels that feature curvatures and branches. Furthermore, the geometric features of the vessels change significantly during normal physiologic movements, such as sitting or walking, thereby subjecting the stent-graft to varying dynamic mechanical stress. Also, the stent-grafts may be subjected to more gradually varying mechanical stresses, such as would occur as gradual changes in the aneurysm morphology occur, such as the shrinkage of the aneurysm.

Therefore, there exists a need for a vascular prosthesis-testing device that more fully simulates the varied physiological stresses induced upon an AAA stent-graft when present in the human body. More specifically, there exists a need for a vascular prosthesis testing device that is operable to induce, in addition to internal fluid pressure stresses, linear compressive, linear tension, torsion, lateral push, and bending stresses, in an oscillatory and/or variable manner, upon a vascular prosthesis.

SUMMARY OF THE INVENTION

In accordance with the present invention, a vascular prosthesis tester for inducing mechanical stresses upon a vascular prosthesis having a channel extending along a longitudinal axis is provided. The vascular prosthesis tester includes a pump adaptable to pressurize a fluid disposed within the channel of the vascular prosthesis to induce a radial strain upon the vascular prosthesis. The tester may further include a bend applicator operable to induce a bending stress upon the vascular prosthesis by bending the vascular prosthesis substantially along the longitudinal axis. The tester may further include a torque applicator operable to induce a torque oriented substantially about the longitudinal axis upon the fluid conduit. The tester may also include a linear force applicator operable to induce a linear force oriented substantially parallel with the longitudinal axis upon the vascular prosthesis.

In accordance with further aspects of the present invention, the vascular prosthesis tester may further include a stop. The stop is operable to engage the fluid conduit and limit the perpendicular displacement of the fluid conduit in at least one direction when the fluid conduit is coupled to the vascular prosthesis tester. In accordance with additional aspects of the present invention, the pump, bend applicator, torque applicator, linear force applicator, and/or stop are operable to induce an oscillatory or gradually varying force or pressure within the channel.

In accordance with the present invention, a method of fatigue testing a vascular prosthesis having an inner channel oriented along a longitudinal axis of the vascular prosthesis is provided. The steps of the method include injecting a pressurized fluid within the inner channel to induce a radial stress upon the vascular prosthesis and inducing a torque, bending stress, and/or linear stress upon the fluid conduit. The torque may be induced substantially about the longitudinal axis. The bending stress may be induced substantially along the longitudinal axis. The linear stress may be induced substantially parallel with the longitudinal axis.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
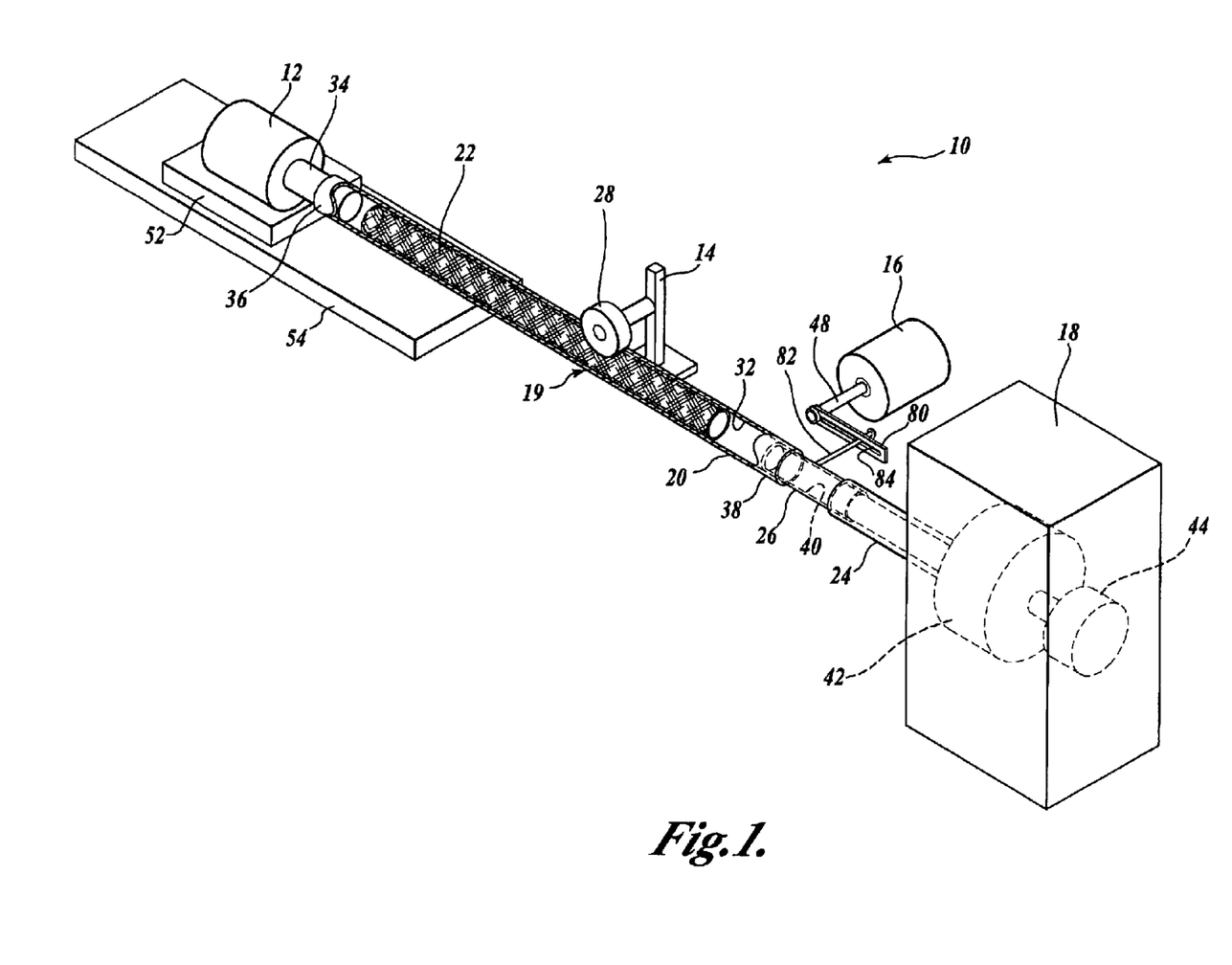
FIG. 1 is a perspective view of one embodiment of a vascular prosthesis tester formed in accordance with the present invention with a portion of a fluid conduit cut-away to reveal a stent-graft contained within the fluid conduit, the fluid conduit shown in relation to a plurality of force applicators.

FIG. 1 illustrates a vascular prosthesis tester 10 formed in accordance with one embodiment of the present invention and suitably used for inducing mechanical stresses upon a vascular prosthesis, such as a stent-graft 22. The illustrated embodiment of the vascular prosthesis tester 10 of the present invention is configured to subject a stent-graft 22 to tensile and/or compressive axial loads, bending stresses, torsional stresses, lateral push stresses, pressure-induced radial strain, and/or fluid shear stresses. The forces may be applied in an oscillatory or gradually varying manner by force applicators or actuators, which may be driven by mechanical, electrical, pneumatic, hydraulic or other suitable means. Further, the actuators may induce the stresses independently or in combination, or in a manner to simulate a physiologic movement, such as walking.

Figure 5:
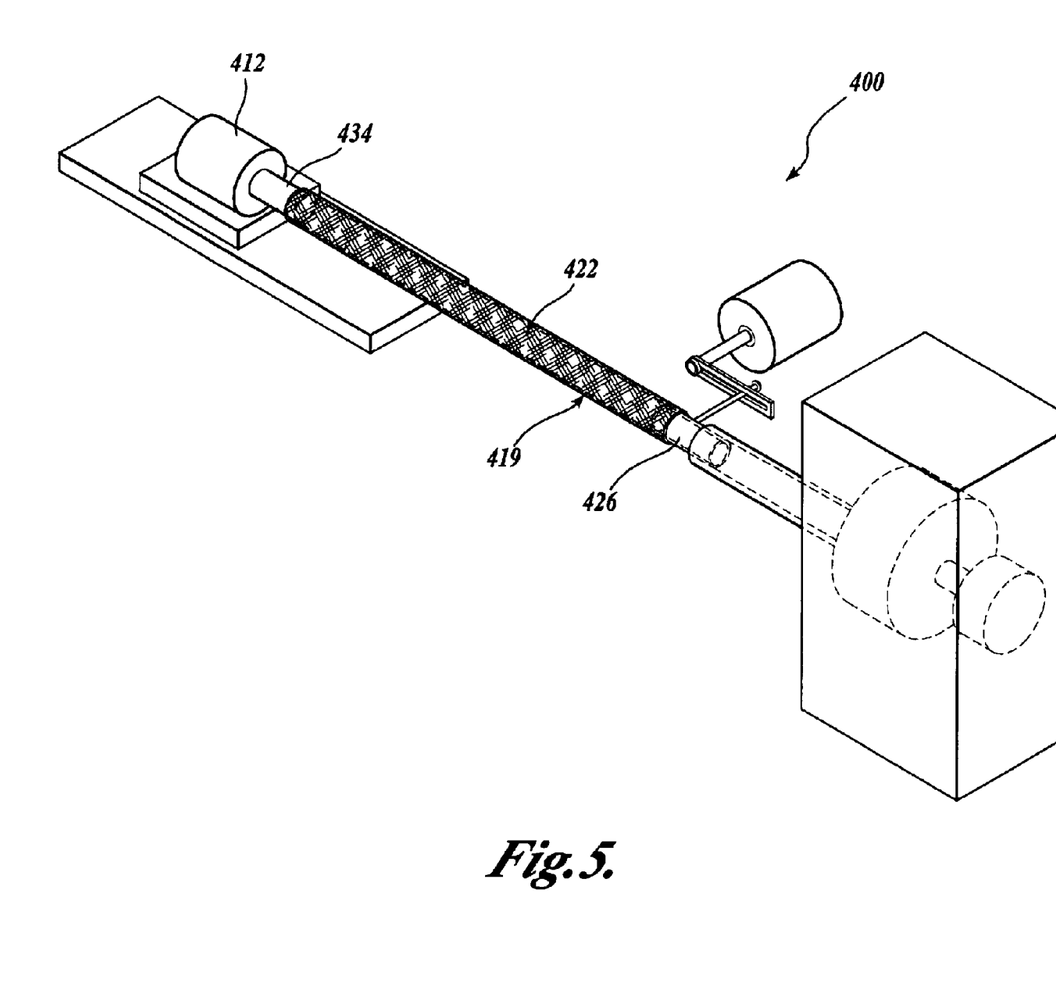
FIG. 5 is a perspective view of a fourth alternate embodiment of a vascular prosthesis tester formed in accordance with the present invention with a stent-graft depicted in relation to a plurality of force applicators.
Figure 6:
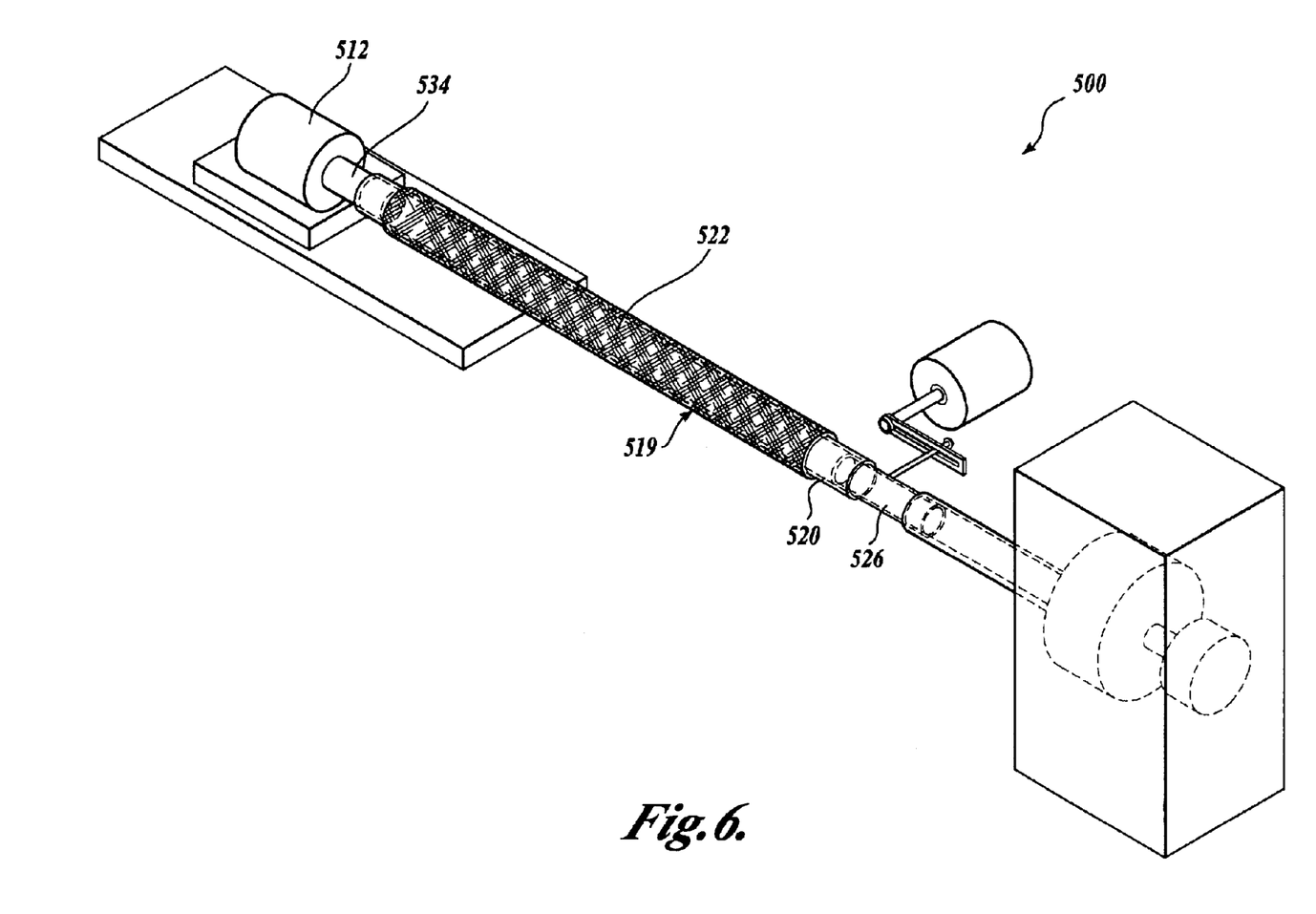
FIG. 6 is a perspective view of a fifth alternate embodiment of a vascular prosthesis tester formed in accordance with the present invention with a stent-graft depicted on the outer surface of a fluid conduit shown in relation to a plurality of force applicators.

The forces are applied upon what, for the purposes of this detailed description, will be generally referred to as a test member. The test member is comprised of a stent-graft 22 and an optional fluid conduit 22, both of which will be described in further detail below. More specifically, the test member may be comprised of stent-graft 22 only, as shown in FIG. 5, a stent-graft 22 disposed on the outer surface of the fluid conduit 20, as shown in FIG. 6, and the stent-graft 22 contained within a channel of the fluid conduit 20, as shown in FIGS. 1–4.

Although the illustrated embodiment of the present invention is described as operable for testing stent-grafts for illustrative purposes, one skilled in the relevant art will appreciate that the disclosed vascular prosthesis tester 10 is suitable for testing other types of vascular prosthesis, such as stents and grafts, for example. Therefore, it should be apparent to one skilled in the art that the vascular prosthesis tester 10 has wide application, and may be used in any situation where subjecting a vascular prosthesis to realistic physiologic mechanical stresses is desirable.

Focusing now on the physical components of the invention, the vascular prosthesis tester 10 includes a torque inducing rotary motor 12, a linear motor 52, a bend-inducing rotary motor 16, a diaphragm pump 18, and a roller 28. The vascular prosthesis tester 10 further includes a test member 19 comprised of a fluid conduit 20 manufactured to recreate the physical properties and characteristics of a vessel intended to receive the stent-graft 22, and a stent-graft 22.

Figure 2:
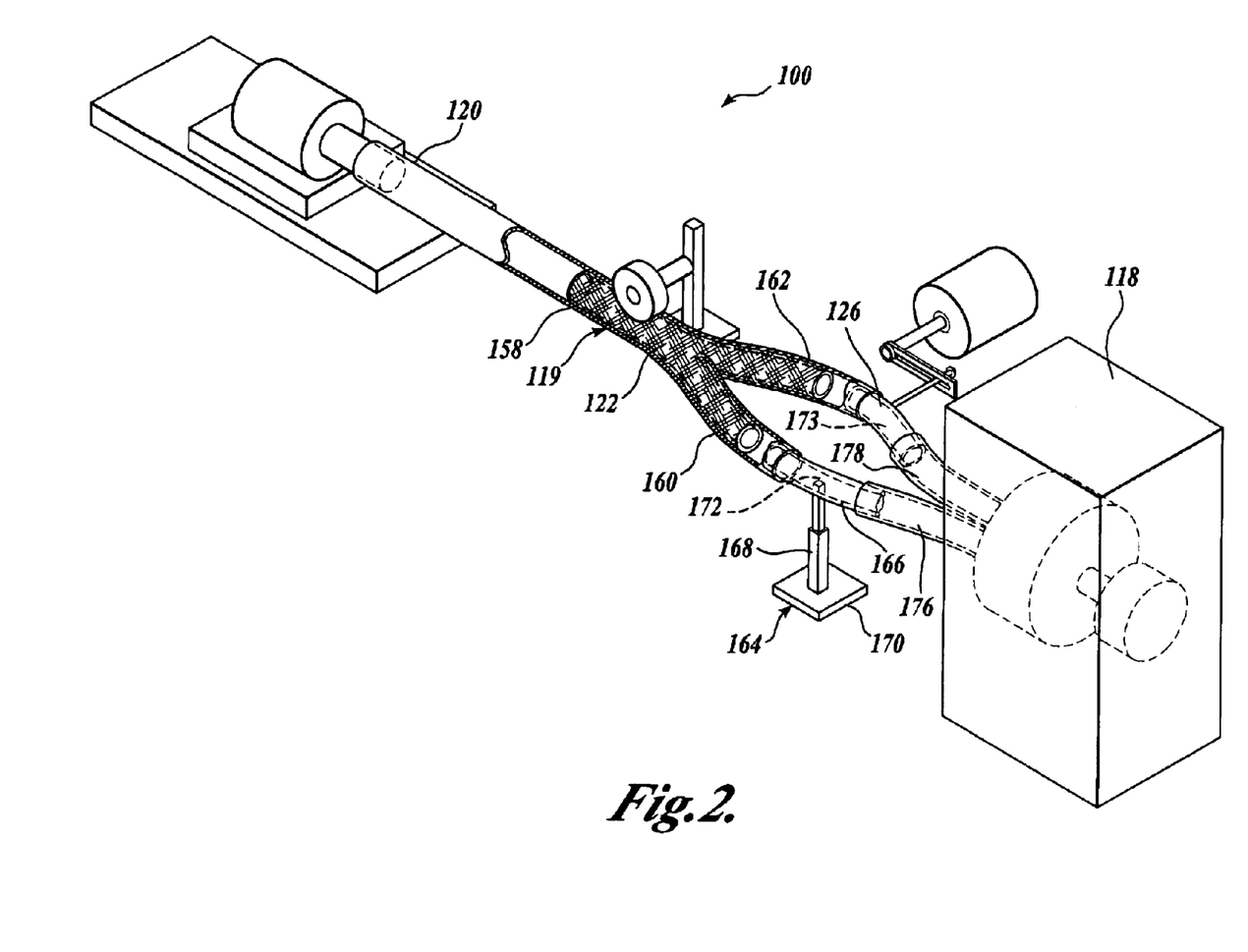
FIG. 2 is a perspective view of a first alternate embodiment of a vascular prosthesis tester formed in accordance with the present invention with a portion of a bifurcated fluid conduit cut-away to reveal a bifurcated stent-graft contained within the bifurcated fluid conduit, the bifurcated fluid conduit shown in relation to a plurality of force applicators.

Focusing now more fully on the fluid conduit 20, the fluid conduit 20 is formed with a longitudinally aligned inner channel 32 for receiving the stent-graft 22 therewithin. In one embodiment of the present invention, the fluid conduit 20 is made of a transparent silicone elastomer. The fluid conduit 20 may be a single straight fluid conduit as shown or a bifurcated or branched fluid conduit such as shown in FIG. 2, selected to correspond with the size and shape of a human aorta. The fluid conduit 20 may be made by casting the material between an inner mandrel made of a polished metal rod, and a removable outer shell in a manner to exhibit compliance representative of a physiological counterpart. Or the fluid conduit 20 may be formed by applying a selected liquid material to a rotating mandrel. Such a method of formation for forming a fluid conduit suitable for use with the present invention is disclosed in Moore et al., *A Device for Subjecting Vascular Endothelial Cells to Both Fluid Shear Stress and Circumferential Cyclic Stretch, Annals of Biomedical Engineering*, Vol. 22, pp. 416–422 (1994).

More specifically, the Moore et al article discloses forming a fluid conduit suitable for use in the present invention by applying a very thin layer (~0.2 mm) of a silicone elastomer, such as the silicone elastomer sold under the trademark SYLGARD® 184 by DOW CORNING®, in a liquid state to a highly polished 6 mm diameter cylinder that is constantly and slowly rotated in an oven at 150° C. The application of liquid silicone elastomer to the mandrel is carefully controlled to ensure that the thickness of the fluid conduit does not vary around the circumference or along the length. The fluid conduit is then allowed to solidify inside the oven, and then is carefully removed from the mandrel.

The inner surface of the fluid conduit 20 may be lined with a grid pattern so that any deformation of the stent-graft 22 occurring during testing may be measured optically. The grid may be produced by machining shallow, narrow grooves in the outer surface of the mandrel. The narrow groves may be filled with black powder, such as printer toner, to provide visual indicia to facilitate optical deformation measuring.

Once the fluid conduit 20 is formed, a stent-graft is placed within the inner channel 32 for testing. The inner diameter of the inner channel 32 is selected to provide a friction fit of the stent-graft 22 within the inner channel 32, so that any force applied to the fluid conduit 20 is also exhibited upon the stent-graft 22. After insertion of the stent-graft 22 within the fluid conduit 20, a first end 36 of the fluid conduit 20 may be rigidly coupled to an axial aligned drive shaft 34 of a rotary motor 12. In one actual embodiment of the present invention, the rotary motor 16 is a four-phase hybrid 1.8-degree step motor, model number 42D225, manufactured by Anaheim Automation, located at 910 East Orangefair Lane, Anaheim, Calif., 92801-1195.

The rotary motor 12 may be computer controlled to induce a torsional stress upon the fluid conduit 20, and thus the stent-graft 22 contained therewithin, by rotation of the drive shaft 34 and thus the attached first end 36 of the fluid conduit 20. The rotary motor 12 may be controlled by computer to apply the torsional stress in an oscillatory manner, having a frequency and amplitude selected by the user. As a non-limiting example, the oscillatory stress may be applied by rotating the first end 36 of the fluid conduit 20 from a neutral position clockwise to a selected angular displacement. The rotary motor 12 may then rotate the first end 36 of the fluid conduit 20 back to the neutral position, or alternatively, rotate the first end 36 to a selected angular displacement in a counterclockwise direction. As should be apparent to one skilled in the art, the cycle may be repeated and varied as desired.

The rotary motor 12 may also apply the torsional stress in a substantially variable manner, where the first end 36 of the fluid conduit 20 is rotated and held at a selected angular displacement. It will be appreciated by one skilled in the art, that the term "variable" and the phrase "gradually varying" used within this detailed description include embodiments where a force is applied and held at a relatively constant level as described above, but also includes embodiments where the force is gradually increased or decreased over a selected time period, the time period being substantially greater than the frequency of oscillatory applied forces.

The vascular prosthesis tester 10 is also capable of inducing linear compressive and tensile stresses upon the fluid conduit 20 and the stent-graft 22. To accomplish this, a linear motor 52 selectively adjusts the longitudinal position of a rigidly attached rotary motor 12, thereby selectively applying linear forces upon the fluid conduit 20. More specifically, the linear motor 52 is a single-axis linear stepper motor that reciprocates in a longitudinal manner along the length of a stationary platen 54 in a direction substantially parallel to the length of the fluid conduit 20. The linear motor 52 is computer controlled to selectively reciprocate along the stationary platen 54, thereby adjusting the linear position of the attached rotary motor 12 to selectively induce linear stresses (either tensile or compressive) upon the fluid conduit 20 and the stent-graft 22 contained therewithin.

The linear stresses may be applied in an oscillatory manner having a frequency and amplitude selected by the user. As a non-limiting example, the oscillatory stress may be applied by extending the linear motor 52 toward the first end 36 of the fluid conduit 20 from a neutral position to a selected extended position, thereby applying compressive forces upon the fluid conduit 20. The linear motor 52 may then retract along the stationary platen 54 back to the neutral position, or alternatively, continue retracting to a selected retracted position, thereby applying a tensile stress upon the fluid conduit 20. The described cycle may be repeated and varied as desired. The linear motor 52 may also apply the stress in a variable manner, where the fluid conduit 20 is induced with a constant (or gradually increasing or decreasing) linear stress. In one embodiment of the present invention, the linear motor 52 is a single-axis linear stepper motor, model number LMSS-1304-2WW1, manufactured by Baldor Electric Company, located at 5711 R. S. Boreham, Jr. St., P.O. Box 2400, Fort Smith, Ariz., 72901.

The vascular prosthesis tester 10 is also operable to apply radial and fluid shear stresses upon a stent-graft. To accomplish this, a second end 38 of the fluid conduit 20 is coupled in fluid communication with the diaphragm pump 18 by a section of flexible tubing 24. The diaphragm pump 18 is controlled to generate a cyclic or oscillating pressure gradient in a fluid, such as a saline solution, contained within the fluid conduit 20 and flexible tubing 24. The oscillating pressure gradient is preferably selected to model the physiologic pressure gradients induced in the arteries of a human by the beating of the heart. A fitting 26, having an inner passageway 40, is used to couple the flexible tubing 24 of the diaphragm pump 18 in fluid communication with the second end 38 of the fluid conduit 20.

Focusing now on the pump 18, the pump 18 includes a diaphragm 42 having the saline solution disposed on a first side of the diaphragm 42, and a driver 44 for driving the diaphragm 42 in a reciprocating manner on a second side of the diaphragm 42. The driver 44 may be reciprocatingly driven by any means known in the art, such as by a linear voice-coil motor 44 as disclosed in U.S. Pat. No. 5,670,708, issued to Vilendrer, the disclosure of which is hereby expressly incorporated by reference. Or alternately, the diaphragm may be mechanically driven, such as by a rotary motor coupled to a rotary to linear conversion component, such as disclosed in U.S. Pat. No. 4,972,721, issued to Conti, the disclosure of which is hereby expressly incorporated by reference.

As the driver 44 reciprocatingly drives the diaphragm 42, saline solution under pressure is injected within the fluid conduit 20, selectively pressurizing the fluid conduit 20. The selective pressurization and depressurization of the fluid conduit 20 induces circumferential (radial) hoop stresses and fluid shear stresses within the fluid conduit 20 and the stent-graft 22 contained therewithin. Although the pump 18 may apply pressure to the fluid conduit 20 in a variable manner, the pump 18 preferably drives the fluid in an oscillatory manner to model the stress applied by a change of blood pressure in a vessel during the pumping of the heart. Therefore, in one embodiment, the diaphragm is configured to provide fluid pressures in the range of 80 to 140 mm of mercury, analogous to the pressures produced by the pumping of the human heart. Further, although the frequency range of biological importance basically lies between 50 and 200 cycles per minute for the human heart, the frequency of the oscillatory application of the pressure gradient in the fluid conduit may be substantially increased above this range to 6,000 cycles per minute or higher to model the forces exerted upon a vascular prosthesis in a shortened period in the lab.

To determine the quantity of days simulated during a period of testing in the lab for a given pump pressure frequency and modeled heart rate, the following formula is used:

$$\text{days simulated} = \text{days tested in lab} \frac{\text{pump pressure frequency}}{\text{normal heart rate}}$$

For example, the stresses induced upon a stent-graft exhibited to an average of 100 beats per minute over a 60 day period may be simulated in one day in the lab when the diaphragm pump is operated at a frequency of 6,000 fluctuations per minute.

The vascular prosthesis tester 10 is also operable to apply bending stresses upon the fluid conduit 20. To accomplish this, the fitting 26 described above for the pump 18 is coupled to a perpendicularly aligned rotary motor 16. The fitting 26 is coupled to the rotary motor 16 via a slotted lever 80 and a torque shaft 82. The slotted lever 80 is an elongate flat bar having a slot 84 longitudinally disposed along the length of the lever 80. The slot 84 is sized to slidingly accommodate the torque shaft 82 therethrough. The torque shaft 82 is coupled to the fitting 26 in a pivotal or rigid manner, depending upon the type of bending stresses desired to be induced upon the fluid conduit 20 and stent-graft 22 contained therewithin.

The rotary motor 16 is computer controlled to rotate, thereby exhibiting the attached fluid conduit 20 and the stent-graft 22 contained within to bending stresses. The rotary motor 16 may be controlled by computer to apply the bending stress in a cyclic or oscillatory manner as selected by the user. As a non-limiting example, the oscillatory bending stresses may be applied by rotating the second end 38 of the fluid conduit 20 from a neutral position clockwise to a selected angular displacement, then rotating back to the neutral position, or alternatively, rotating the second end 38 to a selected angular displacement in a counterclockwise direction. The rotary motor 16 may also apply the bending stress in a variable manner, where the second end 38 is rotated and held at a selected angular displacement, or alternately, the angular displacement gradually increased or decreased. In one embodiment of the present invention, the rotary motor 16 is a four-phase hybrid 1.8-degree step motor, model number 42D225, manufactured by Anaheim Automation, located at 910 East Orangefair Lane, Anaheim, Calif., 92801-1195.

The vascular prosthesis tester 10 is also operable to apply lateral push stresses upon the fluid conduit 20. To accomplish this, a stop in the form of a roller 28 is used in combination with the rotary motor 16. The roller 28 engages the fluid conduit 20, thereby limiting the perpendicular movement of the fluid conduit 20 in a radial direction. As is apparent to one skilled in the art, the roller 28 serves to manipulate the bending forces applied to the fluid conduit 20 in coordination with the perpendicularly aligned rotary motor 16. More specifically, the position of the roller 28 may be adjusted either longitudinally or laterally. By placing the roller 28 longitudinally closer to the rotary motor 16, the radius of curvature of the fluid conduit 20 is increased for a selected angular displacement of the slotted lever 80. Alternately, by placing the roller 28 longitudinally further away from the rotary motor 16, the radius of curvature of the fluid conduit 20 is decreased for a particular angular displacement of the drive disc 46. Further, in resisting the lateral displacement of the fluid conduit 20 during an applied bending stress by the rotary motor 16, the roller 28 applies a later "push" force against the fluid conduit 20. This lateral push force is useful in testing the durability and fatigue characteristics of a stent-graft to such lateral forces. Further, the roller 28 may be reciprocatingly driven to apply lateral push forces independently of the rotary motor 16.

In light of the above description of the various components of the vascular prosthesis tester 10, the operation of the tester 10 will now be discussed. The rotary motors 12 and 16, the linear motor 52, the roller 28, and the diaphragm pump 18, collectively referred to as force applicators or actuators, may induce stresses individually or in various combinations. As discussed above, the force applicators may apply forces in an oscillating fashion to simulate normal physiologic movements, such as cyclic bending to simulate walking, or in a variable manner to simulate gradual changes, such as would be caused by changes in aneurysm morphology. The force applicators used to apply these forces may be electrical, mechanical, pneumatic, or hydraulic, or of other constructs known in the art.

In reference to the diaphragm pump 18, the internal pressure is preferably cycled at a selected, relatively high frequency so that several years of heartbeats can be simulated in a short time frame. At the same time, the other forces mentioned above may be applied to the stent-graft to simulate physiological stresses induced upon the stent-graft by physiologic movements of a human, such as walking. When it is desired to simulate normal physiologic movement, the other forces will be applied cyclically at a frequency that is scaled in proportion to the frequency of the cyclic pressure gradient to correspond to the movement being modeled. For example, the frequency of the application of stresses simulating walking would be calculated by the formula:

$$\text{test frequency} = \text{pressure frequency} \frac{\text{normal step frequency}}{\text{normal heart rate}}$$

For example, if one wishes to model a human walking at the rate of 100 steps per minute, at a heart rate of 150 beats per minute, with the diaphragm pump operating at a pressure frequency of 2000 beats per minute, the actuators simulating the physiological forces of walking would be operated at a frequency of 1333 stresses or cycles per minute. As should be apparent to one skilled in the art, operating under the above parameters, the test device 10 would simulate the stresses induced by a human walking for 13.3 minutes in one minute.

The vascular prosthesis tester 10 includes a well known microprocessor based data acquisition and control system (not shown). Such a system, such as that disclosed in U.S. Pat. No. 5,670,708, issued to Vilendrer, the disclosure of which is hereby expressly incorporated by reference, will allow a user to selectively control and record the stresses induced upon the stent-graft. The system includes a series of transducers. In one embodiment, the data acquisition and control system includes well known pressure, linear displacement, radial displacement and temperature transducers, to facilitate the recordation and production of feedback control signals, and angular displacement transducers to measure the angular displacement of the rotary motors.

The transducers measure the forces applied to the fluid conduit 20. The data acquisition and control system records the data received from the transducers and processes the data to provide actuator control commands in response to the data as is well known in the art. The data acquisition and control system further includes a heating element that is controlled via a closed loop PID control system. The PID control system includes a conventional temperature transducer and heating element coupled to both a microprocessor-based temperature controller and the fluid conduit to maintain the fluid at a selected temperature, such as 37° C.

Figure 3:
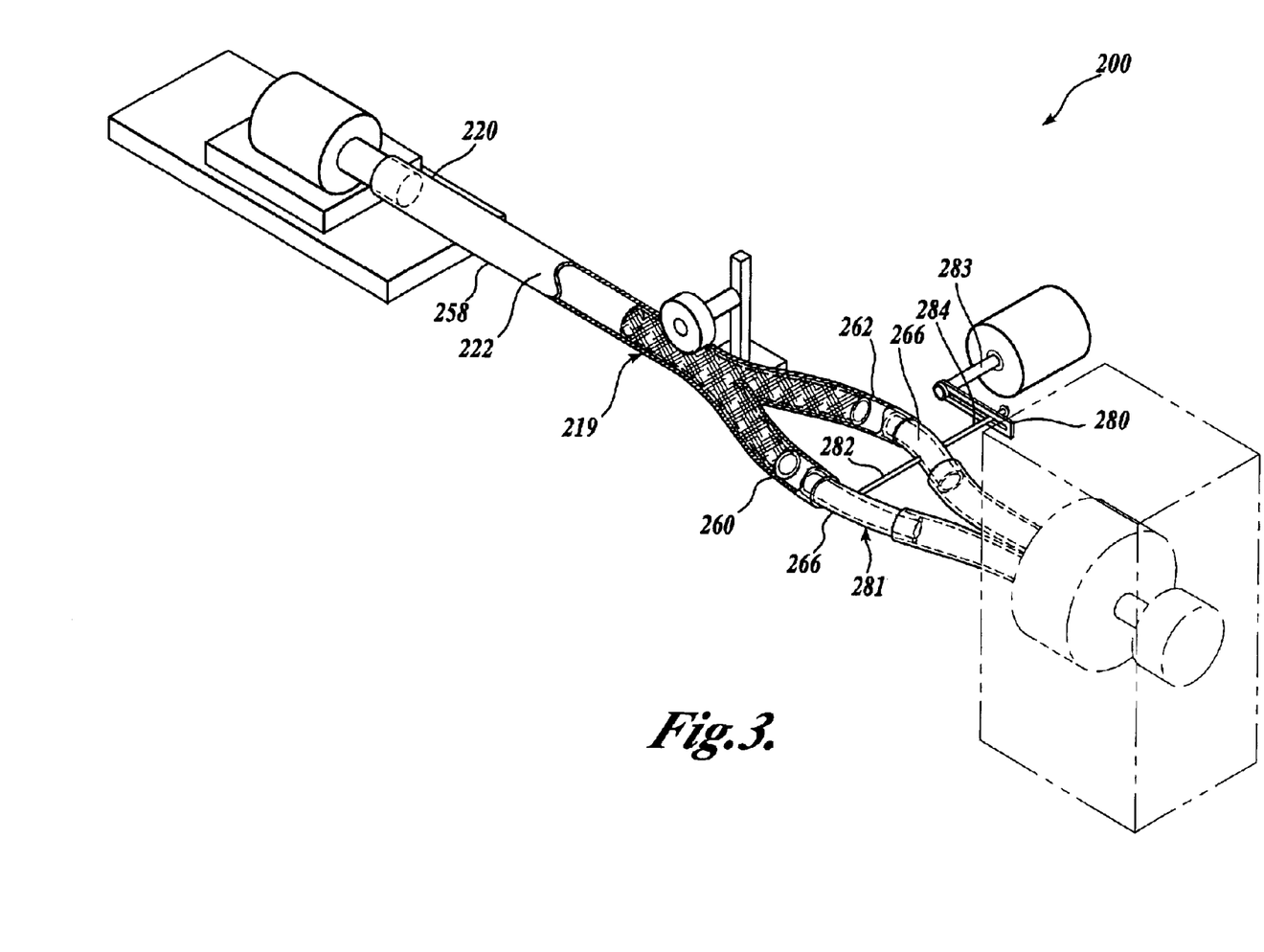
FIG. 3 is a perspective view of a second alternate embodiment of a vascular prosthesis tester formed in accordance
Figure 4:
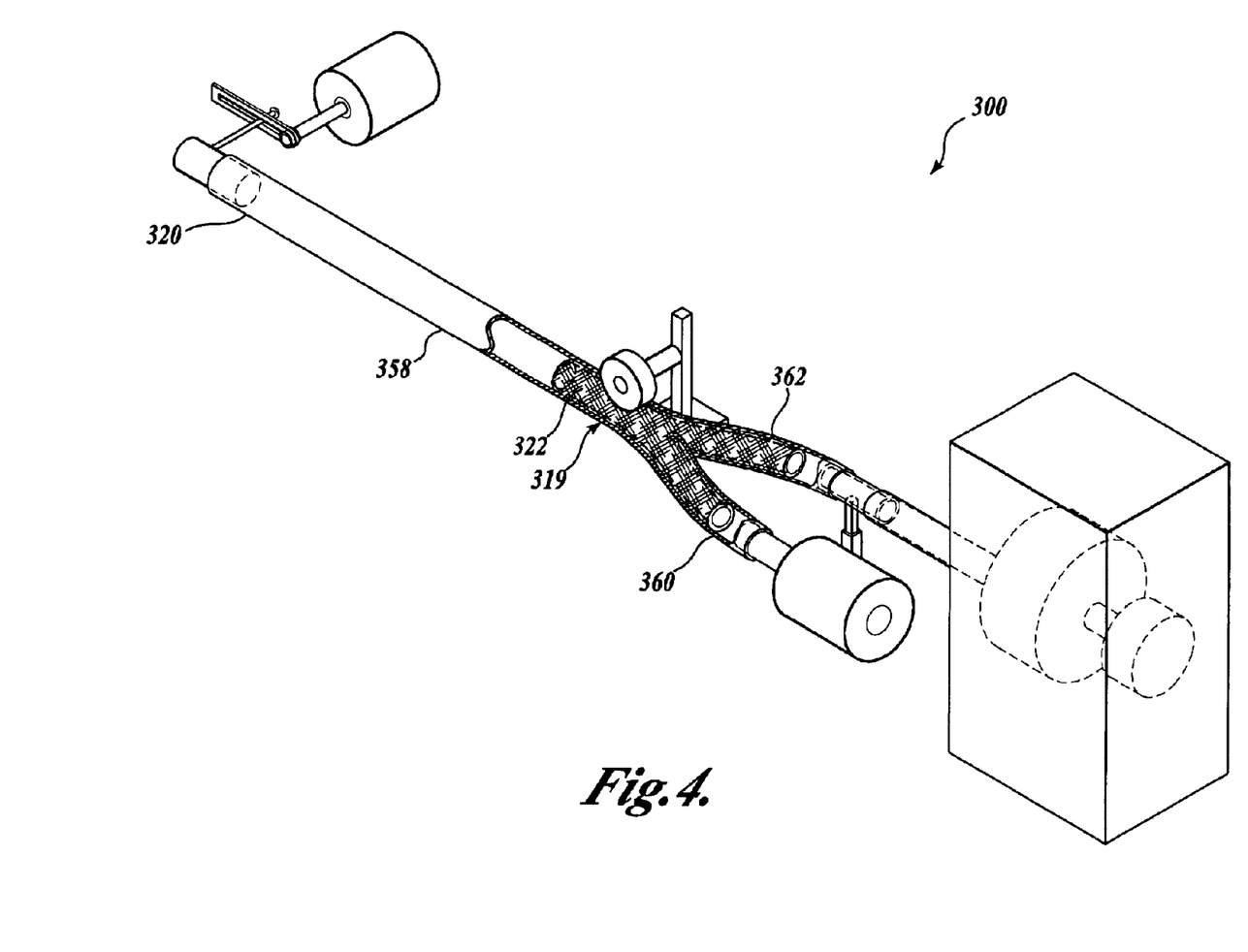
FIG. 4 is a perspective view of a third alternate embodiment of a vascular prosthesis tester formed in accordance with a portion of a bifurcated fluid conduit cut-away to reveal a bifurcated stent-graft contained within the bifurcated fluid conduit, the bifurcated fluid conduit shown in relation to a plurality of force applicators.

Referring now to FIGS. 2–4, three alternate embodiments of vascular prosthesis testers 100, 200, and 300, all formed in accordance with the present invention, will now be described in greater detail. The vascular prosthesis testers 100, 200, and 300 are substantially similar in materials and operation as the embodiment described above in FIG. 1, with the exception that the vascular prosthesis testers depicted in FIGS. 2–4 have been modified to test bifurcated vascular prosthesis, such as a bifurcated stent-graft 122, 222, and 322. The bifurcated stent-graft is comprised of a main channel that divides into a first and a second branch. The bifurcated stent-graft is placed within a similarly shaped fluid conduit 120, 220, and 320 having a main channel 158, 258, and 358 and a first branch 160, 260, and 360 and a second branch 162, 262, and 362, to form branched test members 119, 219, and 319.

Inasmuch as there are now three portions of the fluid conduit 120, 220, and 320 for attaching force actuators thereupon, it should be apparent to one skilled in the art that the possible testing configurations is significantly increased. Although some exemplary examples of possible configurations will be described following, it should be apparent to one skilled in the art the disclosed embodiments are exemplary in nature, and other testing configurations are suitable for use and within the scope of the present invention.

Referring to FIG. 2, in a first alternate embodiment, the first branch 160 of the fluid conduit 120 is coupled to a fixed conduit adapter 164. The fixed conduit adapter 164 serves to rigidly suspend an end of the fluid conduit 120 during testing. The fixed conduit adapter 164 is comprised of a generally horizontal oriented cylinder 166 attached to a telescoping extension arm 168. The extension arm 168 is coupled to a base 170 for rigidly supporting the extension arm 168 as it supports the cylinder 166 in a stable and stationary manner a selected distance above a surface (not shown). The extension arm 168 is adjustable in length to allow the height of the cylinder 166 to be selectively adjusted. Alternately, the cylinder 166 may be reciprocatingly driven to apply lateral push forces and/or bending forces upon the fluid conduit 120.

The cylinder 166 has an outer diameter selected to sealing engage the inner surface of the first branch 160 of the fluid conduit 120. The sealing engagement of the cylinder 166 with the first branch 160 may be enhanced with a suitable device, such as a sealing compound, O-ring disposed in an annular channel on the fixed conduit adapter, or a well known mechanical fastener. A longitudinal fluid passageway 172 passes through the cylinder 166 of the fixed conduit adapter 164. The passageway 172 allows the passage of a pressurized fluid generated in a diaphragm pump 118 to pass through the cylinder 166 and into the fluid conduit 120.

Once installed, a first end of the cylinder 166 is coupled to the first branch 160 of the fluid conduit 120. A second end of the cylinder 166 is coupled to a tube 176 coupled to the diaphragm pump 118. Thus, a fluid pulse generated in the diaphragm pump 118 passes through the tube 176 and through the passageway 172 in the cylinder 166, and into the first branch 160 of the fluid conduit 120, thereby exhibiting radial and fluid shear stresses upon the fluid conduit 120 and the stent-graft 122 contained therein. Likewise, a fluid pulse generated in the diaphragm pump 118 may simultaneously pass through a second tube 178 through a longitudinal fluid passageway 173 in a fitting 126 and into the second branch 162 of the fluid conduit 120.

Although the embodiment depicted in FIG. 2 is described as having passageways 172 and 173 in both the cylinder 166 of the fixed conduit adapter 164 and the fitting 126, it should be apparent to one skilled in the art that the passageways 172 and 173 may be selectively configured so that either, neither, or one of the passageways 172 allow the passage of a fluid therethrough, depending on the needs of the user. If both passageways 172 are eliminated or blocked, then diaphragm pump 118 and the diaphragm pump's associated tubes 176 and 178 may also be eliminated.

The operation and physical make-up of the remaining components of the vascular prosthesis tester 100 are substantially similar to that described above for the vascular prosthesis tester 10 of FIG. 1, and therefore will not be described in further detail herein.

Referring to FIG. 3, a second alternate embodiment of a vascular prosthesis tester 200 formed in accordance with the present invention will now be described in greater detail. The vascular prosthesis tester 200 is substantially similar in materials and operation as the embodiment described above and depicted in FIG. 2, with the exception that vascular prosthesis tester 200 has been modified to simultaneously apply a bend stress to both a first and a second branch 260 and 262 of a fluid conduit 220 containing a bifurcated stent-graft 222.

To aid in applying simultaneous bend stresses to both a first and a second branch 260 and 262 of the fluid conduit 220, a bifurcated conduit adapter 281 is used. The bifurcated conduit adapter 281 is comprised of two cylinders 266 both rigidly (or alternately pivotally) coupled to a shaft 282 oriented generally perpendicular to the length of the cylinders 266. A driven portion 284 of the shaft 282 extends outward and generally perpendicular to the length of the cylinders 266. The driven portion 284 interfaces with a slotted lever 280 coupled to a distal end of a drive shaft 283 of a rotary bend motor 216, in an identical manner as to that described for the embodiment depicted in FIG. 1.

Referring to FIG. 4, a third alternate embodiment of a vascular prosthesis tester 300 formed in accordance with the present invention will now be described in greater detail. The vascular prosthesis tester 300 is substantially similar in materials and operation as the embodiment described above and depicted in FIG. 2, with the exception that the vascular prosthesis tester 300 has been modified to apply a bending stress to a main channel 358 of a fluid conduit 320 while applying a torque stress to a first branch 360 of the fluid conduit 320 containing a bifurcated stent-graft 322.

Referring to FIG. 5, a fourth alternate embodiment of a vascular prosthesis tester 400 formed in accordance with the present invention will now be described in greater detail. The vascular prosthesis tester 400 is similar in materials and operation as the embodiment described above and depicted in FIG. 1, with the exception that a test member 419 of the vascular prosthesis tester 400 does include a fluid conduit. More specifically, a first end of the vascular prosthesis, such as a stent-graft 422, directly and sealingly engages a drive shaft 434 of a rotary motor 412. Likewise, a second end of the stent-graft 422 directly and sealing engages a fitting 426. Configured as such, the need for a fluid conduit to house the stent-graft 422 is eliminated. As should be apparent to one skilled in the art, the concept of having a test member wherein the fluid conduit has been eliminated, and attaching the stent-graft 422 directly to the force actuators, is not limited to the testing configuration depicted in FIG. 5, but has wide application, and is suitable for any testing configuration, including but not limited to those depicted in FIGS. 1–4.

Referring to FIG. 6, a fifth alternate embodiment of a vascular prosthesis tester 500 formed in accordance with the present invention will now be described in greater detail. The vascular prosthesis tester 500 is substantially similar in materials and operation as the embodiment described above and depicted in FIG. 1, with the exception that a test member 519 is comprised of a fluid conduit 520 inserted within the tubular core of a vascular prosthesis, such as a stent-graft 522, such that the stent-graft 522 now envelopes the fluid conduit 520. More specifically, a first end of the fluid conduit 520 directly and sealingly engages a drive shaft 534 of a rotary motor 512. A second end of the fluid conduit 520 directly and sealing engages a fitting 526. Inasmuch as the stent-graft 522 engages the outer surface of the fluid conduit 520, any bending stresses, torque stresses, linear compressive or tensile stresses, or hoop stresses exhibited upon the fluid conduit are also exhibited upon the stent-graft 522. As should be apparent to one skilled in the art, the concept of forming a test member by placing the stent-graft upon the exterior of the fluid conduit is not limited to the testing configuration depicted in FIG. 6, but has wide application, and is suitable for any testing configuration, including but not limited to those depicted in FIGS. 1–4.

While the preferred embodiment of the invention has been illustrated and described, it will be appreciated that various changes can be made therein without departing from the spirit and scope of the invention.

What is claimed is:

1. A vascular prosthesis tester for inducing mechanical stresses upon a test member, the test member comprising a channel extending along a longitudinal axis and a vascular prosthesis, the vascular prosthesis tester comprising:

(a) a pump adaptable to couple in fluid communication with the test member to pressurize a fluid disposed within the channel to induce a radial strain upon the vascular prosthesis; and (b) a bend applicator operable to engage the test member to induce a bending stress upon the vascular prosthesis by bending the test member substantially along the longitudinal axis.

2. The vascular prosthesis tester of claim 1, wherein the pump is operable to induce an oscillating fluid pressure upon the fluid disposed within the channel.

3. The vascular prosthesis tester of claim 1, wherein the bend applicator is operable to induce an oscillating bending stress upon the vascular prosthesis.

4. The vascular prosthesis tester of claim 1, further comprising a torque applicator operable to engage the test member to induce a torque oriented substantially about the longitudinal axis upon the vascular prosthesis.

5. The vascular prosthesis tester of claim 4, wherein the torque applicator is coupled to a linear force applicator operable to induce linear movement to the torque applicator substantially parallel with the longitudinal axis to thereby apply a linear force oriented substantially parallel with the longitudinal axis upon the vascular prosthesis.

6. The vascular prosthesis tester of claim 1, further comprising a linear force applicator operable to induce a linear force oriented substantially parallel with the longitudinal axis upon the vascular prosthesis.

7. The vascular prosthesis tester of claim 1, further comprising a stop operable to engage the test member to impede perpendicular movement of the vascular prosthesis in at least one direction at a location spaced from the bend applicator.

8. The vascular prosthesis tester of claim 1, wherein the test member is comprised of a fluid conduit having a passageway extending along the longitudinal axis, wherein the passageway is operable to receive the vascular prosthesis therewithin, and wherein the fluid conduit is adaptable to couple in fluid communication with the pump and engage the bend applicator.

9. The vascular prosthesis tester of claim 1, wherein the test member is comprised of a fluid conduit having a passageway extending along the longitudinal axis wherein the fluid conduit is operable to be at least partially disposed within an inner channel of the vascular prosthesis, and wherein the fluid conduit is adaptable to couple in fluid communication with the pump.

10. The vascular prosthesis tester of claim 1, wherein the test member is comprised of a branched fluid conduit having a branched passageway extending through the branched fluid conduit, wherein the branched passageway is operable to receive a branched vascular prosthesis therewithin, and wherein the branched fluid conduit is adaptable to couple in fluid communication with the pump and engage the bend applicator.

11. The vascular prosthesis tester of claim 1, wherein the pump and the bend applicator are adaptable to couple to a first end of the test member.

12. The vascular prosthesis tester of claim 11, further comprising a torque applicator operable to couple to a second end of the test member to induce a torque oriented substantially about the longitudinal axis upon the vascular prosthesis.

13. A vascular prosthesis tester for inducing mechanical stresses upon a test member, the test member comprising a channel extending along a longitudinal axis and a vascular prosthesis, the vascular prosthesis tester comprising:
  (a) a pump adaptable to couple in fluid communication with the test member to inject a pressurized fluid within the channel to induce a radial strain upon the vascular prosthesis; and
  (b) a torque applicator operable to engage the test member to induce a torque oriented substantially about the longitudinal axis upon the vascular prosthesis.

14. The vascular prosthesis tester of claim 13, wherein the pump is operable to induce an oscillating fluid pressure within the channel.

15. The vascular prosthesis tester of claim 13, wherein the torque applicator is operable to induce an oscillating torque stress upon the vascular prosthesis.

16. The vascular prosthesis tester of claim 13, wherein the torque applicator is operable to engage a first end of the test member and the pump is operable to couple in fluid communication with a second end of the test member.

17. The vascular prosthesis tester of claim 13, wherein the torque applicator is coupled to a linear force applicator operable to induce linear movement to the torque applicator substantially parallel with the longitudinal axis to thereby apply a linear force oriented substantially parallel with the longitudinal axis upon the vascular prosthesis.

18. The vascular prosthesis tester of claim 13, further comprising a bend applicator operable to engage the test member to induce a bending stress substantially along the longitudinal axis by bending the vascular prosthesis.

19. The vascular prosthesis tester of claim 13, further comprising a linear force applicator operable to induce a linear force oriented substantially parallel with the longitudinal axis upon the vascular prosthesis.

20. The vascular prosthesis tester of claim 13, further comprising a stop operable to engage the test member to impede perpendicular movement of the vascular prosthesis in at least one direction.

21. The vascular prosthesis tester of claim 13, wherein the test member is comprised of a fluid conduit having a passageway extending along the longitudinal axis, wherein the passageway is operable to receive the vascular prosthesis therewithin, and wherein the fluid conduit is adaptable to couple in fluid communication with the pump and engage the torque applicator.

22. The vascular prosthesis tester of claim 13, wherein the test member is comprised of a fluid conduit having a passageway extending along the longitudinal axis, wherein the fluid conduit is operable to be at least partially disposed within an inner channel of the vascular prosthesis, and wherein the fluid conduit is adaptable to couple in fluid communication with the pump and engage the torque applicator.

23. The vascular prosthesis tester of claim 13, wherein the test member is comprised of a branched fluid conduit having a branched passageway extending through the branched fluid conduit, wherein the branched passageway is operable to receive a branched vascular prosthesis therewithin, and wherein the branched fluid conduit is adaptable to couple in fluid communication with the pump and engage the torque applicator.

24. A vascular prosthesis tester for inducing mechanical stresses upon a test member having a channel extending along a longitudinal axis and a vascular prosthesis, the vascular prosthesis tester comprising:
  (a) a pump adaptable to couple in fluid communication with the test member to inject a pressurized fluid within the channel to induce a radial strain upon the vascular prosthesis; and
  (b) a linear force applicator operable to induce linear forces oriented substantially parallel with the longitudinal axis upon the vascular prosthesis, wherein the linear force applicator is adapted to selectively vary a magnitude of the linear forces induced in the test member during testing of the test member.

25. The vascular prosthesis tester of claim 24, wherein the pump is operable to induce an oscillating fluid pressure within the channel.

26. The vascular prosthesis tester of claim 24, wherein the linear force applicator is operable to induce an oscillating linear force upon the vascular prosthesis.

27. The vascular prosthesis tester of claim 24, wherein the pump is adaptable to couple to a first end of the test member and the linear force applicator is operable to induce the linear forces upon a second end.

28. The vascular prosthesis tester of claim 24, further comprising a torque applicator coupled to the linear force applicator, wherein the linear force applicator is operable to induce linear movement to the torque applicator to thereby apply the linear forces.

29. The vascular prosthesis tester of claim 24, further comprising a bend applicator operable to engage the test member to induce a bending stress upon the vascular prosthesis by bending the test member substantially along the longitudinal axis.

30. The vascular prosthesis tester of claim 24, further comprising a torque applicator operable to engage the test member to induce a torque oriented substantially about the longitudinal axis upon the vascular prosthesis.

31. The vascular prosthesis tester of claim 24, further comprising a stop operable to engage the test member to impede perpendicular movement of the test member in at least one direction.

32. The vascular prosthesis tester of claim 24, wherein the test member is comprised of a fluid conduit having a passageway extending along the longitudinal axis, wherein the passageway is operable to receive the vascular prosthesis therewithin, and wherein the fluid conduit is adaptable to couple in fluid communication with the pump and be engaged by the linear forces induced by the linear applicator.

33. The vascular prosthesis tester of claim 24, wherein the test member is comprised of a fluid conduit having a passageway extending along the longitudinal axis, wherein the fluid conduit is operable to be at least partially disposed within an inner channel of the vascular prosthesis, and wherein the fluid conduit is adaptable to couple in fluid communication with the pump and to be engaged by the linear forces induced by the linear force applicator.

34. The vascular prosthesis tester of claim 24, wherein the test member is comprised of a branched fluid conduit having a branched passageway extending through the branched fluid conduit, wherein the branched passageway is operable to receive the vascular prosthesis therewithin, and wherein the branched fluid conduit is coupled in fluid communication with the pump and engaged by the linear forces induced by the linear force applicator.

35. A vascular prosthesis tester for inducing mechanical stresses upon a test member, the test member comprising a channel extending along a longitudinal axis and a vascular prosthesis, the vascular prosthesis tester comprising:

(a) a pump adaptable to couple in fluid communications with the test member to pressurize a fluid disposed within the channel to induce a radial stress upon the vascular prosthesis;

(b) a bend applicator operable to engage the test member to induce a bending stress upon the vascular prosthesis by bending the test member substantially along the longitudinal axis;

(c) a torque applicator operable to engage the test member to induce a torque oriented substantially about the longitudinal axis upon the vascular prosthesis; and (d) a linear force applicator operable to induce a linear force oriented substantially parallel with the longitudinal axis upon the vascular prosthesis.

36. The vascular prosthesis tester of claim 35, wherein the pump is further comprised of a diaphragm adaptable to have the fluid disposed on a first side of the diaphragm, and a driver coupled to the diaphragm for driving the diaphragm in a reciprocating manner, thereby permitting the selective pressurization of the fluid.

37. The vascular prosthesis tester of claim 35, wherein the bend applicator is comprised of a rotary motor having a driven member that rotates on an axis oriented substantially perpendicular to the longitudinal axis, wherein the driven member is operable to apply a bending stress upon the vascular prosthesis by bending the vascular prosthesis substantially along the longitudinal axis.

38. The vascular prosthesis tester of claim 35, wherein the torque applicator is comprised of a rotary motor having a driven member that rotates on an axis oriented substantially parallel to the longitudinal axis, wherein the driven member is operable to couple to the test member to apply a torque upon the vascular prosthesis.

39. The vascular prosthesis tester of claim 35, wherein the linear force applicator is comprised of a linear actuator operable to apply tensile and compressive linear forces aligned substantially parallel with the longitudinal axis upon the vascular prosthesis.

40. The vascular prosthesis tester of claim 35, wherein the pump is operable to induce an oscillating fluid pressure within the channel.

41. The vascular prosthesis tester of claim 35, wherein the bend applicator is operable to induce an oscillating bending stress upon the vascular prosthesis.

42. The vascular prosthesis tester of claim 35, wherein the torque applicator is operable to induce an oscillating torque upon the vascular prosthesis.

43. The vascular prosthesis tester of claim 35, wherein the linear force applicator is operable to induce an oscillating linear force upon the vascular prosthesis.

44. The vascular prosthesis tester of claim 35, wherein the pump is adaptable to couple in fluid communication to a first end of the test member and the torque applicator is operable to couple to a second end of the test member.

45. The vascular prosthesis tester of claim 35, wherein the torque applicator is coupled to the linear force applicator, wherein the linear force applicator is operable to induce linear movement of the torque applicator to thereby apply the linear force.

46. The vascular prosthesis tester of claim 35, wherein the pump and the bend applicator are operable to couple to a first end of the test member and the torque applicator is operable to engage a second end of the test member.

47. The vascular prosthesis tester of claim 35, wherein at least one from the group consisting of the pump, bend applicator, torque applicator, and linear force applicator are operable to apply a variable stress upon the vascular prosthesis and one from the group consisting of the pump, bend applicator, torque applicator, and linear force applicator are operable to apply an oscillating stress upon the vascular prosthesis.

48. The vascular prosthesis tester of claim 35, further comprising a stop operable to engage the test member to impede perpendicular movement of the vascular prosthesis in at least one direction.

49. The vascular prosthesis tester of claim 35, wherein the test member is comprised of a fluid conduit having a passageway extending along a longitudinal axis, wherein the passageway is operable to receive the vascular prosthesis therewithin, and wherein the fluid conduit is adaptable to couple in fluid communication with the pump.

50. The vascular prosthesis tester of claim 35, wherein the test member is comprised of a fluid conduit having a passageway extending along a longitudinal axis, wherein the fluid conduit is operable to be at least partially disposed within an inner channel of the vascular prosthesis, and wherein the fluid conduit is adaptable to couple in fluid communication with the pump.

51. The vascular prosthesis tester of claim 35, wherein the test member is comprised of a branched fluid conduit having a branched passageway extending through the branched fluid conduit, wherein the branched passageway is operable to receive a branched vascular prosthesis therewithin, wherein the fluid conduit is adaptable to couple in fluid communication with the pump.

52. A method of fatigue testing a test member comprising an inner channel oriented along a longitudinal axis and a vascular prosthesis, the method comprising:
   (a) injecting a pressurized fluid within the inner channel to induce a radial stress upon the vascular prosthesis; and
   (b) inducing a bending stress oriented substantially along the longitudinal axis upon the vascular prosthesis.

53. The method of claim 52, wherein the fluid is injected by a pump coupled in fluid communication to a first end of the test member.

54. The method of claim 52, wherein the bending stress is applied by a bend applicator coupled to a first end of the test member.

55. The method of claim 52, further comprising inducing a torque oriented substantially about the longitudinal axis upon the vascular prosthesis.

56. The method of claim 52, wherein the torque is induced by a torque applicator comprised of a rotary motor adaptable to couple to a second end of the test member.

57. The method of claim 52, further comprising inducing a linear force oriented substantially along the longitudinal axis upon the vascular prosthesis.

58. The method of claim 52, wherein the linear force is applied by a linear force actuator operable to move an adapter coupled to the test member along the longitudinal axis to induce a linear stress in the vascular prosthesis.

59. A method of fatigue testing a test member comprising an inner channel oriented along a longitudinal axis and a vascular prosthesis, the method comprising:
   (a) injecting a pressurized fluid within the inner channel to induce a radial stress upon the vascular prosthesis; and
   (b) inducing a torque upon the vascular prosthesis oriented substantially about the longitudinal axis.

60. The method of claim 59, wherein the fluid is injected by a pump coupled in fluid communication to a first end of the test member.

61. The method of claim 60, wherein the torque is applied by a torque applicator coupled to a second end of the test member.

62. The method of claim 59, further comprising inducing a bending stress oriented substantially along the longitudinal axis upon the vascular prosthesis.

63. The method of claim 59, wherein the bending stress is induced by a bend applicator comprised of a rotary motor adaptable to couple to a first end of the test member.

64. The method of claim 59, further comprising inducing a linear force oriented substantially along the longitudinal axis upon the vascular prosthesis.

65. The method of claim 59, wherein the linear force is applied by a linear force actuator operable to move an adapter coupled to the test member along the longitudinal axis to induce a linear stress in the vascular prosthesis.

66. A method of fatigue testing a test member comprising an inner channel oriented along a longitudinal axis and a vascular prosthesis, the method comprising:
   (a) injecting a pressurized fluid within the inner channel to induce a radial stress upon the vascular prosthesis; and
   (b) applying a linear force upon the vascular prosthesis oriented substantially along the longitudinal axis, wherein a magnitude of the linear force is selectively varied during testing of the test member.

67. The method of claim 66, wherein the linear force is applied by a linear force actuator operable to move an adapter coupled to the test member along the longitudinal axis to induce a linear stress in the vascular prosthesis.

68. The method of claim 66, further comprising inducing a bending stress oriented substantially along the longitudinal axis upon the vascular prosthesis.

69. The method of claim 66, wherein the bending stress is induced by a bend applicator comprised of a rotary motor adaptable to couple to a first end of the test member.

70. The method of claim 66, further comprising inducing a torque oriented substantially about the longitudinal axis upon the vascular prosthesis.

71. The method of claim 66, wherein the torque is applied by a torque applicator coupled to a second end of the test member.

* * * * *

UNITED STATES PATENT AND TRADEMARK OFFICE
CERTIFICATE OF CORRECTION

PATENT NO. : 6,810,751 B2
DATED : November 2, 2004
INVENTOR(S) : M.R. Moreno et al.

It is certified that error appears in the above-identified patent and that said Letters Patent is hereby corrected as shown below:

Title page,
Item [*] Notice, "143 days." should read -- 148 days. --

Signed and Sealed this

First Day of March, 2005

JON W. DUDAS
*Director of the United States Patent and Trademark Office*